United States Patent
Pereira

(10) Patent No.: US 12,211,605 B2
(45) Date of Patent: Jan. 28, 2025

(54) DEVICE, SYSTEM AND METHOD FOR STORING CLINICAL-SURGICAL DATA

(71) Applicant: Ricardo Mendes Alves Pereira, São Paulo (BR)

(72) Inventor: Ricardo Mendes Alves Pereira, São Paulo (BR)

(*) Notice: Subject to any disclaimer, the term of this patent is extended or adjusted under 35 U.S.C. 154(b) by 53 days.

(21) Appl. No.: 17/048,210

(22) PCT Filed: Apr. 16, 2019

(86) PCT No.: PCT/BR2019/050137
§ 371 (c)(1),
(2) Date: Oct. 16, 2020

(87) PCT Pub. No.: WO2019/200445
PCT Pub. Date: Oct. 24, 2019

(65) Prior Publication Data
US 2021/0158928 A1    May 27, 2021

(30) Foreign Application Priority Data

Apr. 16, 2018 (BR) .................. 102018007667-1

(51) Int. Cl.
*G16H 20/40* (2018.01)
*G06F 21/62* (2013.01)
*G16H 30/20* (2018.01)

(52) U.S. Cl.
CPC ......... *G16H 20/40* (2018.01); *G06F 21/6245* (2013.01); *G16H 30/20* (2018.01)

(58) Field of Classification Search
CPC ...... G16H 40/40; G16H 20/40; G06T 7/0014; A61B 17/16; A61B 5/0022; A61B 1/3132;
(Continued)

(56) References Cited

U.S. PATENT DOCUMENTS 6,633,328 B1 * 10/2003 Byrd .................. A61B 90/30
                                                    348/E7.087
8,313,432 B2    11/2012 Chiu et al.
(Continued)

FOREIGN PATENT DOCUMENTS

CA    2386829 C  *  6/2012  .......... G11B 27/034
EP    0215604 A2    3/1987
(Continued)

OTHER PUBLICATIONS

Google patents search, Mar. 24, 2022 (Year: 2022).*
(Continued)

*Primary Examiner* — Dilek B Cobanoglu
(74) *Attorney, Agent, or Firm* — Laurence P. Colton; Smith Tempel Blaha LLC

(57) ABSTRACT

The present invention describes a device, a system, and a process for storing clinical-surgical data from clinical-surgical environment. Specifically, the present invention comprises an integrating means provided with a processor capable of receiving clinical-surgical data from a plurality of signal sources and for generating integrated and resized data to promote the storage of such data, providing a high degree of security in order to prevent frauds or damage to data/signals generated in the clinical-surgical event. The present invention pertains to the fields of health, medicine, and information technology.

14 Claims, 12 Drawing Sheets

(58) Field of Classification Search
CPC ....... A61B 90/30; A61B 90/36; G11B 27/034; G06F 21/6254; H04N 19/172
USPC .......................................... 705/2–3; 600/210
See application file for complete search history.

(56) References Cited

U.S. PATENT DOCUMENTS

| | | | |
|---|---|---|---|
| 8,687,226 B2 | 4/2014 | Samari | |
| 8,882,662 B2 * | 11/2014 | Charles | A61B 17/16 600/210 |
| 9,552,660 B2 * | 1/2017 | Tripathi | G06T 7/0014 |
| 9,642,606 B2 * | 5/2017 | Charles | G16H 40/63 |
| 10,019,819 B2 * | 7/2018 | Tripathi | A61B 5/745 |
| 10,806,325 B2 * | 10/2020 | Miller | H04N 19/172 |
| 10,893,917 B2 * | 1/2021 | Wade | A61B 1/3132 |
| 2006/0270913 A1 | 11/2006 | Todd | |
| 2007/0120763 A1 * | 5/2007 | De Paepe | G06F 3/14 345/1.3 |
| 2007/0271122 A1 * | 11/2007 | Zaleski | G16H 40/67 705/3 |
| 2008/0235052 A1 | 9/2008 | Node-Langlois et al. | |
| 2009/0216556 A1 * | 8/2009 | Martin | G16H 40/63 705/3 |
| 2011/0276340 A1 * | 11/2011 | DeBoer | G16H 40/40 705/2 |
| 2013/0201273 A1 * | 8/2013 | Renzi | H04N 7/141 348/14.01 |
| 2016/0220324 A1 * | 8/2016 | Tesar | G02B 21/0012 |
| 2016/0253472 A1 | 9/2016 | Pedersen | |
| 2016/0314716 A1 * | 10/2016 | Grubbs | G09B 23/306 |
| 2017/0020627 A1 * | 1/2017 | Tesar | A61B 90/361 |
| 2017/0143852 A1 * | 5/2017 | Gao | C08F 8/30 |
| 2018/0042680 A1 * | 2/2018 | DiMaio | G16H 20/40 |
| 2018/0336500 A1 * | 11/2018 | Pinho | G16H 80/00 |
| 2019/0354200 A1 * | 11/2019 | Rapoport | A61B 90/36 |

FOREIGN PATENT DOCUMENTS

| | | | |
|---|---|---|---|
| EP | 2296596 B1 * | 1/2017 | ............. A61B 90/20 |
| EP | 3506289 A1 * | 7/2019 | ......... G06F 21/6254 |
| ES | 2264845 A1 * | 1/2007 | ........... A61B 5/0002 |
| WO | WO-2016149794 A1 * | 9/2016 | ........... A61B 5/0022 |

OTHER PUBLICATIONS ip.com search, Mar. 24, 2022 (Year: 2022).*

Discrete cosine transform domain image resizing using correlation of discrete cosine transform coefficients, Min-Kyoung Cho Byung-Uk Lee, Ewha W. University, Department of Information Electronics, Journal of Electronic Imaging 15(3), 033009 (Jul.-Sep. 2006) (Year: 2006).*

Towards a mouth gesture based laparoscope camera command, J.B. Gomez; F. Prieto; T. Redarce, Published in: 2008 International Workshop on Robotic and Sensors Environments, Rose 2008—IEEE International Workshop on Robotic and Sensors Environments (Year: 2008).*

WIPO, International Search Report (in a related application), Jul. 2, 2019.

* cited by examiner

FIG. 4d

DEVICE, SYSTEM AND METHOD FOR STORING CLINICAL-SURGICAL DATA

FIELD OF THE INVENTION

This invention describes a solution capable of collecting data/signals generated during a clinical-surgical event and of concentrating such information in a device. Said device is provided in a safe way with a high degree of security in order to prevent fraud or damage to data/signals generated in the clinical-surgical event. The present invention pertains to the fields of health, medicine, and information technology.

BACKGROUND OF THE INVENTION

In the field of health, there are several issues to be broadly and widely discussed and analyzed. In the case of clinical settings, like hospitals, wards, operating rooms, medical offices, there is a great need to perform processes as safely as possible in order to provide the appropriate care to patients. In this case, any type of procedure that may occur improperly can cause great harm to the patient and the health system as a whole.

The inconveniences that can occur in clinical settings are diverse, ranging from a failure in surgical equipment to a human failure. Unfortunately, many of these failures occur and are not always detected, reported, or documented and therefore not further analyzed. Currently, there are no practical solutions on the market aimed at assisting in the capture and documentation of information from surgical environments.

The prior art related to the present invention includes the following documents:

US 2006/0270913 entitled "Surgical Console Operable to Record and Playback a Surgical Procedure". Such document discloses a system and method for programming a surgical console to perform a surgical procedure involving several steps. The parameters recorded from a surgical procedure may be subsequently used in other procedures.

EP 0215604 entitled "Video and Analogue Data Recording System". Said document discloses a system and method for recording and streaming two different signals, such video and an analog signal representing biological data. A processor receives a patient's analog signal and a video signal from a camera, and combines these two signals into a single synchronized data stream.

U.S. Publ. Appl. No. 2008/0235052 entitled "System and Method for Sharing Medical Information Between Image-Guided Surgery Systems". Said document discloses an expert system and method for accessing, storing and sharing medical information from an imaging device for use during the planning and performance of surgical procedures.

U.S. Pat. No. 8,313,432 entitled "Surgical Data Monitoring and Display System". Said document discloses a system for monitoring and presenting surgical data, which includes (i) a data storage module for storing surgical data in real time or retrospectively; (ii) a first processor module for receiving and processing the retrospective surgical data; and (iii) a second processor module for receiving and processing surgical data in real time. Said modules transmit the processed data to different monitors before or during a medical or surgical procedure.

U.S. Pat. No. 8,687,226 entitled "Medical Data Recording System". Said document discloses a device for recording information on CDs or other recording media, and for printing information from medical files, like X-ray images, magnetic resonance images etc.

U.S. Publ. Appl. No. 2016/0253472 entitled "Surgical Data Control System". Said document discloses a system comprising a wireless data receiver for receiving surgical data transmitted wirelessly from surgical instruments, drug delivery equipment, and a power system for surgical equipment. Medical data is recorded in a memory system and may give rise to reports containing general data of a surgery. Such reports may be transmitted to a network as soon as the surgery is completed.

WO 2016/149794 entitled "Operating Room Black-box Device, System, Method and Computer Readable Medium for Event and Error Prediction". Said document discloses a multichannel recorder/encoder for gathering, integrating, synchronizing and recording medical or surgical data received as independent streams of real-time medical or surgical data from a plurality of hardware units. Examples of hardware units include a control unit, cameras, sensors, audio devices, and patient monitoring devices.

However, the prior art solutions run in a severely complex way. In addition, the known systems do not aim to provide much security for gathered/stored data. It is noteworthy that clinical/surgical data is extremely important, so that any external interference, whether attempted fraud or damage to the data itself, can have irreparable consequences for a patient's health as well as for future audits performed for the stored event. In this sense, the prior art fails to provide a solution that allows a high degree of security for the data generated during a clinical/surgical event.

From the searched literature, no documents were found anticipating or suggesting the teachings of the present invention, so that the solution proposed here presents novelty and inventive activity against the prior art.

SUMMARY OF THE INVENTION

The present invention has the object to solve the problems found in the prior art by developing a solution capable of collecting the data/signals generated during a clinical-surgical event and concentrating such information in a device. Said device is securely provided with a high degree of security in order to prevent fraud or damage to data/signals generated from the clinical-surgical event. Thus, clinical-surgical data is stored in a safe way with restricted access to one or more event operators or managers, where such data can be safely reproduced and analyzed later.

In a first object, the present invention provides a device for storing clinical-surgical data from at least one clinical-surgical event, wherein the device comprises at least one integrating means (10) configured to receive clinical-surgical data from a plurality of signal sources (20), wherein the integrating means (10) is provided with at least one processor (11) which gathers the clinical-surgical data received by the integrating means (10), and the said processor (11) has at least one block for resizing and composing the clinical and surgical data.

In a second object, the present invention provides a system for storing clinical-surgical data from at least one clinical-surgical event comprising:
 a. at least one signal source (20);
 b. at least one storage device (1) for clinical-surgical data, said device as defined above; and
 C. at least one remote storage (30);
wherein said storage device (1) is in communication with the signal source (20) and the remote storage (30).

In a third object, the present invention provides a process for storing clinical-surgical data from at least one clinical-surgical event, comprising the steps of:

a. receiving clinical and surgical data by at least one integrating means (10) arranged in a data storage device (1), the clinical-surgical data originating from at least one signal source (20);
b. resizing the clinical-surgical data received by at least one processor (11) disposed on the storage device (1);
c. the processor (11) sending the resized and composite clinical-surgical data to at least one of: image display (13); local storage (12); remote storage (30); or a combination of them.

The inventive concept common to all claimed protection contexts refers to the integration of clinical-surgical data from different sources and to generate the integrated data to store it in a storage medium. The solution of the present invention, unlike the others of the prior art, brings a stand-alone device that does not depend on the local structure for the storage medium. The device stores the data in its own storage medium with redundancy. During the event, the device allows that instant photos (snapshots) be taken of the images being acquired by triggering the specific interface for this purpose.

These and other objects of the invention will be immediately appreciated by those skilled in the art and companies having an interest in the segment, and will be described in sufficient detail for their reproduction in the following description.

BRIEF DESCRIPTION OF THE DRAWINGS

In order to better define and clarify the contents of this patent application, the following figures are presented.

DETAILED DESCRIPTION OF THE INVENTION

Figure 1:
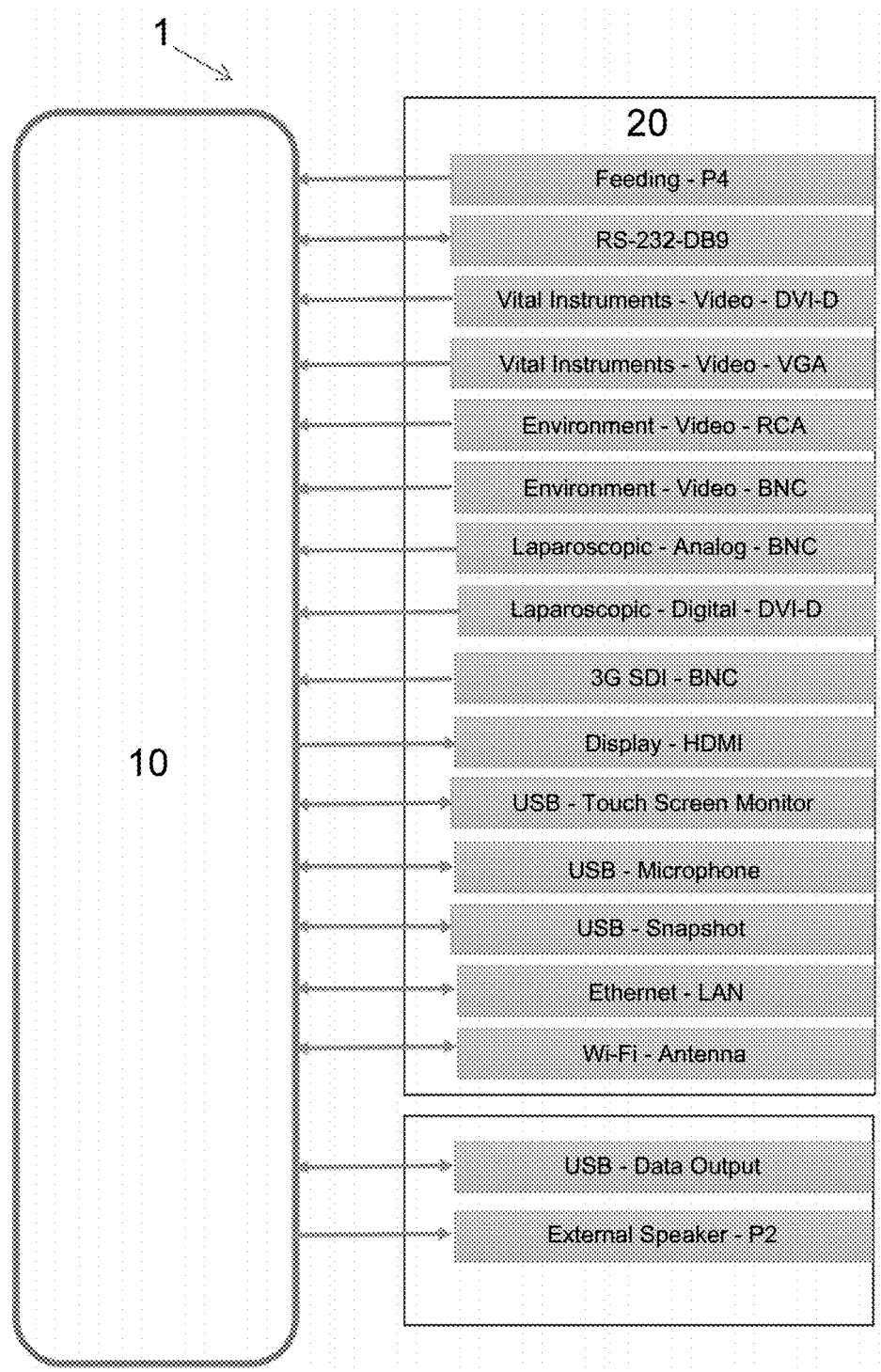
FIG. 1 shows a diagram of an embodiment of the storage device (1) of the present invention, showing the integrating means (10) and some examples of signal sources (20).

The following descriptions are given by way of example and not to limit the scope of the invention, but to provide a more clear understand of the subject matter of the present patent application.

The present invention provides a solution for performing the storage of clinical-surgical data provided in clinical-surgical environments, such that these clinical-surgical data can be reproduced and analyzed.

In a first object, the present invention presents a storage device (1) for clinical-surgical data from at least one clinical-surgical event, wherein the device comprises at least one integrating means (10) configured to receive clinical-surgical data from a plurality of signal sources (20), wherein the integrating means (10) is provided with at least one processor (11) which gathers the clinical-surgical data received by the integrating means (10), said processor (11) having at least one resizing and composition block of clinical-surgical data. Thereby, the storage device (1) of the present invention may be locally installed in a clinical-surgical environment in order to collect and store information from the signal sources (20) present in the clinical-surgical environment. For example, a clinical-surgical environment is any environment where any clinical-surgical procedure can be performed, for example, hospitals, wards, ambulances, operating rooms, medical offices etc.

In one embodiment, the processor (11) of the integrating means (10) is configured to interpret the different communication protocols adopted by the different signal sources (20) from the clinical-surgical environment, thereby resizing and composing the information through the resizing block. In another embodiment, the processor (11) of the integrating means (10) comprises a standard data entry protocol, so that the signal sources (20) from the clinical-surgical environment are already adapted to transfer data from such protocol, said resizing and composition block being adapted to sequence the information for later distribution. Thus, said processor (11) is responsible for resizing the clinical-surgical data to compose information with this data to be later forwarded to some other element.

In one embodiment where the clinical-surgical data is video signals, the resizing block of the processor (11) is responsible for resizing the incoming video signals in the integrating means (10), and adjusting the respective resolutions for the composition of a new image containing the video signals.

For purposes of example, the integrating means (10) has the function of multiplexing signals from different sources and outputting a sequence of information that can be read and interpreted.

In one embodiment, the signal sources (20) are defined by at least one of: a laparoscopic surgical camera, a vital sign monitor video, an operating room camera, surgical event ambient audio, or a combination thereof. In other words, the signal source (20) is any equipment in a clinical-surgical environment with data related to the clinical-surgical procedure performed.

Further, in one embodiment, the integrating means (10) comprises several clinical-surgical data inputs, these being adapted to be connected to signal sources (20). Thus, data/signals from signal sources (20) are directed to the processor (11) for execution of predefined processes.

Furthermore, said storage device (1) comprises at least one local storage (12) in communication with the processor (11), wherein the local storage (12) is configured to receive and store clinical-surgical data from the processor. (11). Said local storage (12) is any locally installed element in the storage device (1) capable of receiving, storing and making electronic data available upon request. For purposes of illustration, the local storage (12) is a memory device, such as an external or internal HD, with SSD technology, among others.

In one embodiment, the storage device (1) further comprises at least one redundant storage, which is mirrored with respect to the local storage (12) and also locally installed on the storage device (1). Said redundant storage is a memory device, which may be the same as local storage (12) or different, capable of storing data from processor (11). In one embodiment, the redundant storage operates in parallel with the local storage (12), so that the processor (11) sends the clinical-surgical data simultaneously to the local storage (12) and the redundant storage.

In this regard, there is also provided an alarm system implemented in the processor (11) that is capable of detecting and alerting the user/operator of the device in case of: i) proximity of storage depletion of the local storage (either in the local storage (12) or on the redundant storage); and/or ii) failure of the local storage (12), the redundant local store or the transfer of data to the remote storage (30).

The clinical-surgical data storage device (1) of the present invention also enables captured, integrated, and scaled data to be made available for a user to view locally and remotely. Thus, it is provided a video board capable of receiving the resized, composite, and synchronized data by the processor (11) and sending it to an image display which is capable of reproducing the clinical-surgical data on video. In this regard, an image display (13) is connected to the storage device (1) so that a device user can view the available content locally.

In one embodiment, the storage device (1) comprises an image capture element (photograph) adapted for image capture made available on an image display (13) and also on the local storage (12) in a separate file of the images, said image capture element being implemented in the processor (11). The proposed image capture element performs the acquisition of one or more frames available in the image display (13), for example through a freeze snapshot of the displayed video (e.g. photography).

Furthermore, in one embodiment, the image capture element is an algorithm implemented in the processor (11) capable of capturing the frames of the image display (13), this capture being previously defined by a user. For example, capture may occur when predicted action occurs in the clinical-surgical event by triggering an interface device. In another embodiment, the image capture element is an algorithm implemented in processor (11) capable of capturing image display frames by some user action. For example, the image is captured when a user sends a command to the storage device (1).

This image capture element was developed to facilitate some actions of the device users, so that it allows one to easily obtain specific images that occur during the clinical-surgical event. For example, a professional accompanying the event performs the action of capturing images for the preparation of reports, where these images are exported in a format compatible with the report system or the clinical-surgical environment.

Furthermore, in one embodiment, the processor (11) further comprises a logger capable of identifying and storing the actions performed by the users who operated the data storage device (1) of the present invention. In one embodiment, the logger uses the local storage (12) to record user information. In one embodiment, users are classified at different levels of access and/or permission. Log records make it possible to identify which user performed the respective task, allowing a user who tried to commit fraud relative to the clinical-surgical event to be identified.

Additionally, in one embodiment, the storage device (1) comprises a security locking mechanism. Said locking mechanism is provided to increase the security level for accessing the device of the present invention, thereby avoiding human interference in the event of attempted fraud.

Moreover, the data storage device (1) of the present invention further comprises, in one embodiment, a single device operator interaction key, for example, a start/stop key. This single interaction key makes it possible to prevent an operator, as an unauthorized user for configuring the device, from attempting to fraudulently tamper with the recording of the clinical-surgical event.

In a second object, the present invention presents a system for storing clinical-surgical data, derived from at least one clinical-surgical event, comprising: at least one signal source (20); at least one storage device (1); and at least one remote storage (30). In one embodiment, the storage device (1) is as defined above.

The plurality of signal sources (20) is in communication with the storage device (1) wherein the data generated by the sources is transmitted to the device, for example, by wire or wirelessly. In one embodiment, the plurality of signal sources (20) comprises at least one laparoscopic surgical camera, at least one vital sign monitor video, at least one operating room camera, and at least one audio input for recording the audio of the clinical-surgical environment.

By the way of example, without limiting the scope of the invention, a surgical camera refers to any element capable of capturing images from a laparoscopic clinical-surgical procedure. A multiparameter monitor and the BIS module provide vital signs and refer to any element that centralizes the vital information of the patient undergoing the clinical-surgical procedure. All data contained in the respective screen and from the BIS module, the level of consciousness, EMG and SR are imported from the multiparametric monitor. Since the monitor has several acquisition channels, in addition to the signals of heart rate, pressure (systolic and diastolic), oximetry and oxicapnography, some more signals can also be inserted. The operating room camera is any element capable of capturing images of the clinical environment where the clinical-surgical procedure is performed. Audio input is any element capable of capturing the sound of the clinical-surgical environment where the procedure is performed.

The storage device (1), in turn, integrates the received data for scaling and composition through the processor (11). The resized data is stored locally and sent to an image display (13) that is in communication with the storage device (1). The fact that the image display (13) receives the resized and composite data allows the information collected by the storage device (1) to be made available in a single piece of equipment, in a single video image, i.e., it allows all of the information to be easily accessible to the healthcare professional conducting a clinical procedure.

The remote storage (30) is in communication with the storage device (1) enabling the clinical-surgical data to be stored remotely. In one embodiment, the clinical-surgical data is stored remotely after the clinical-surgical event has ended. The storage device (1) makes use of a wired or radio signal (Wi-Fi) connection, e.g. internet, for communication with the said remote storage (30) and thus sends the clinical-surgical data to the remote storage (30).

In one embodiment, the remote storage (30) stores all generated data in all events performed, creating a database with the information obtained. In one embodiment, remote storage (30) is a server located outside of the clinical-surgical environment. In one embodiment, the remote storage (30) is a cloud server capable of receiving data via an internet connection and can be accessed via a web page with login and password needed for access. In one embodiment, the remote storage (30) makes the data available for cloud viewing via browser (web browser—e.g. Google Chrome® or Firefox®); which enables the user to view clinical-surgical data remotely.

In one embodiment, the system further comprises an output interface, for example, USB, which makes it possible to transfer data from storage device (1) to another local or portable storage mechanism.

In one embodiment, the system is provided with an image capture trigger mechanism (snapshot) during the event, implemented in the processor (11). In one embodiment, said trigger mechanism is a foot pedal, which is positioned close to the system operator/user, enabling capture commands to be performed quickly and easily.

In a third object, the present invention provides a process for storing clinical-surgical data from at least one clinical-surgical event, comprising the steps of: i) receiving clinical-surgical data by at least one integrating means (10) arranged in a data storage device (1), the clinical-surgical data being sourced from at least one signal source (20); ii) resizing the clinical and surgical data received by at least one processor (11) arranged on the storage device (1); and iii) the processor (11) sending the resized and composite clinical-surgical data to at least one of: image display (13); local storage (12); remote storage (30); or a combination of them.

After receiving the clinical-surgical data generated by the signal sources (20), the processor (11) initiates a resizing algorithm for the clinical-surgical data to integrate the information from the signal sources (20), composing them in a single block of data synchronized and sequenced to be properly interpreted by other elements. In an embodiment, the clinical-surgical data are video signals, so that the processor (11) resizes the images and composes them into a single image.

Thus, in one embodiment, clinical-surgical data is sent in parallel to the image display (13) and the local storage (12) so that it can be made available to an operator/user and safely stored at the same time. In one embodiment, clinical-surgical data is additionally sent in parallel to the redundant storage, increasing the security level of the generated data.

In one embodiment, processor (11) sends clinical-surgical data to remote storage (30) after completion of the clinical-surgical event. This procedure allows the storage device (1) to have its processing dedicated to store the data generated in the clinical-surgical event in question, avoiding any kind of failure or overload of the processing. In one embodiment, the processor (11) deletes the stored clinical-surgical data after the data is completely sent to the remote storage (30) to free up space in the local storage (12). For this, the processor (11) executes checking routines to verify that the data has been completely transferred to the remote store (30).

Additionally, in one embodiment, the processor (11) initiates a user profiling step, making it possible to configure access and/or permission levels to perform tasks on the storage device (1). Moreover, in one embodiment, the processor permits logs to be generated from the tasks performed by tying the tasks to the user who performed them. This step makes it possible to achieve a higher level of security by identifying the user in the event of attempted fraud or attempting to delete/remove clinical-surgical data stored in local storage (12) or remote store (30).

In addition, the processor (11) is configured to perform an algorithm that makes it possible to perform a step of capturing the images made available on the image display (13). The image capture step comprises the acquisition of one or more frames provided in the image display (13), for example through an instant freezing of the displayed video.

In one embodiment, said image capture step is performed automatically by the processor, considering a predefined configuration, for example, with a user defining the time interval at which this step is performed, or when some predefined action occurs during the event. Predefined actions can be, for example, a failure in some system video input signal, a power outage alert, a specific situation occurring during the surgical event, where this situation can be identified by reading the video available on the display (13) or an action reported during the clinical-surgical procedure etc.

In another embodiment, said image capture (photography) step may be performed by an operator sending a command signal to the storage device (1), this command being read by the processor (11) to capture the display image. Said operator command may be given, for example, by means of a drive mechanism external to, but in communication with, the storage device (1) located next to the operator. In one embodiment, the drive mechanism is a pedal located near the operator.

In one embodiment, processor (11) performs monitoring of the local storage (12) and the redundant storage. Thus, the processor (11) is configured to perform an alarm step indicating to the operator/user when detecting: i) proximity of local store storage capacity exhaustion (either in the storage (12) or the redundant storage); and/or ii) failure of the local storage (12), the redundant local store or the transfer of data to remote store (30). This step is configurable by the device user, making it possible to set considerable limits on storage capacity and/or the types of failures at which the processor issues an alarm.

The solution proposed in the present invention enables the content resulting from a clinical-surgical procedure to be stored and monitored, allowing any eventual failures that occur during the procedure to be stored and to be analyzed later. For instance, such solution enables a user or healthcare professional to analyze the entire contents of the clinical-surgical procedure locally or remotely. In the case of analysis in local mode, the display is responsible for providing the information of the clinical and surgical procedure. In the case of remote analysis, the cloud storage medium is responsible for loading the saved data and by means of a browser (web browser that allows viewing of stored events—e.g. Google Chrome® or Firefox®), for reproducing the information when requested.

Example 1. Application in Surgical Environments

The examples shown herein are intended solely to exemplify one of several ways for carrying out the invention; however, with no limitation to the scope thereof is intended.

The present system has been applied in surgical environments in such a way as to allow all contents relating to a clinical-surgical procedure to be stored by the storage device. Thus, a healthcare professional was able to perform the appropriate analysis on the events that occurred during the clinical-surgical procedure. In this application, signal sources (20) are video signal sources.

As shown in FIG. 1, the storage device (1) contains physical means that provide different clinical data entry standards, the ambient camera (analog) can be connected by video or network (digital) port input, network connection input, vital sign monitor input (VGA or DVI-D) and BIS module (RS-232) etc. In the embodiment of FIG. 1 the following input connectors are shown: Power Input (P4), Vital instruments (DVI-D or VGA), surgical environment video (RCA-S-VIDEO or BNC or IP camera), Digital laparoscopic (DVI-D and 3G-SDI/HD-SDI), cloud connection (Wi-Fi and Ethernet), Audio (P2/USB-Microphone), keyboard (USB-Touch Keyboard/Mouse) and snapshot (USB Pedal).

The device of this embodiment of the invention has the following output elements: Network Interface (Ethernet and Wi-Fi), Data Transfer Interface (USB), Display Interface (FIDMI), Audio (Internal Speaker, P2-External Speaker). Also, said display interface is provided with touch screen technology, allowing the user to alternatively use a mouse and/or an alphanumeric keyboard for the operation of the interface.

In addition, the storage device comprises: mirrored storage discs, security lock to prevent unauthorized opening and a battery for operation in case of power failure.

The storage device also comprises a start/stop button on the touch screen display configured to start stop recording the data gathered by the integrating means (10). In addition, the device is suitable for operation on events lasting from 1 min to 30 hours.

Figure 2:
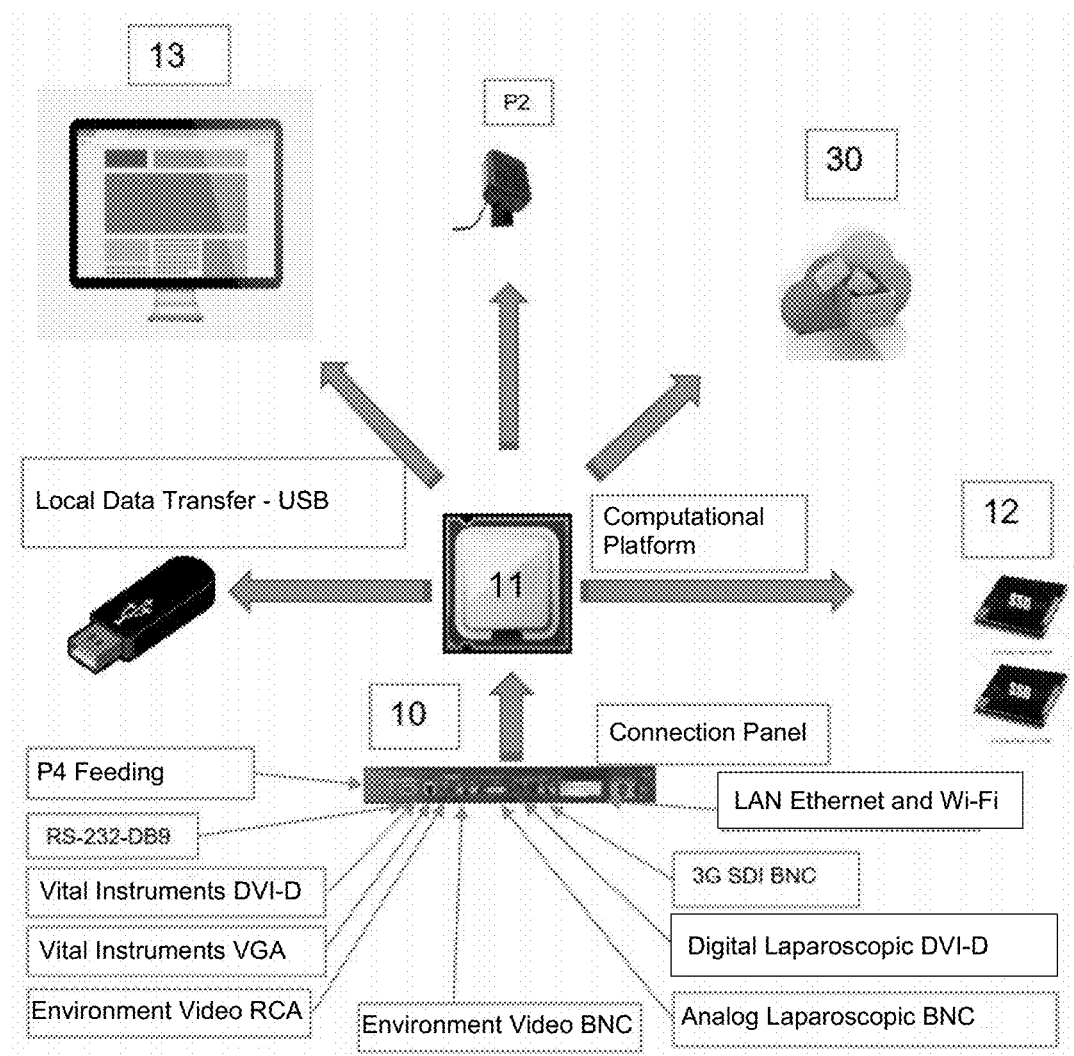
FIG. 2 shows a diagram of an embodiment of the interface system in the present invention, in an overview and with some examples of possible signal sources (20).

FIG. 2 refers to the system as a whole, as implemented in the surgical environment where, as can be seen, the monitoring camera, microphone, laparoscopic procedure camera and vital signal monitor are interconnected with the integrating means. The integrating means (10) is in turn connected to the local storage system (12) and sends integrated data to the redundant storage and cloud storage (30) via Ethernet connection. Stored integrated data can either be analyzed by a healthcare professional in case of failure analysis, as used as educational content. In cases of use for educational purposes, for example, this data is presented to a group of students, where all information on the clinical and surgical procedure is available.

Further, the processor (11) implemented in the integrating means (10) comprises firmware (FW) that includes drivers and support for the operating system, along with several software modules (SW) that meet the various functionality specified for the equipment, performing audio and video capture and compression, storage (local and cloud), data encryption, user interface for accessing data, among others.

Thus, the processor (11) has been configured to receive the video signals from the integrating means (10), where each video signal has its respective resolution, all of them being of the same resolution (e.g. full HD) or all of them in different resolutions. In this sense, the video signals are identified by the resizing block of the processor (11) and are subjected to a resolution adjustment so that they can later be reproduced in a single video image on a display. In this implementation the display had a full HD resolution (i.e. 1920×1080) and thus the input video signals were adjusted to be reproduced in blocks to compose a full HD image. In order to resize the input videos, downscaling algorithms were implemented in the processor (11) itself.

Figure 3:
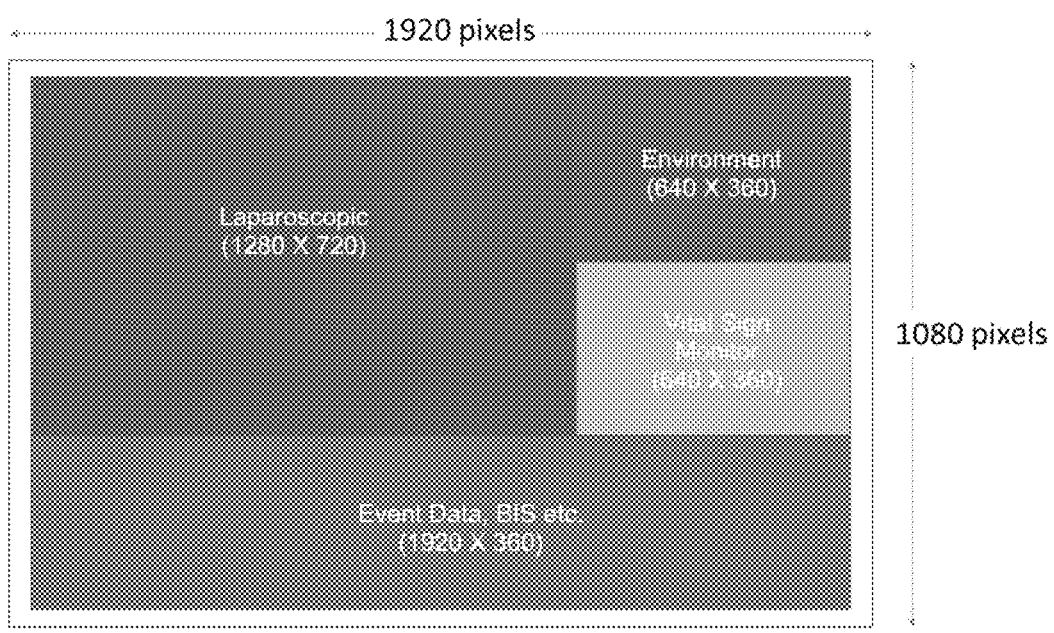
FIG. 3 shows an embodiment of resized and composite clinical-surgical data in a single image.
Figure 4A:
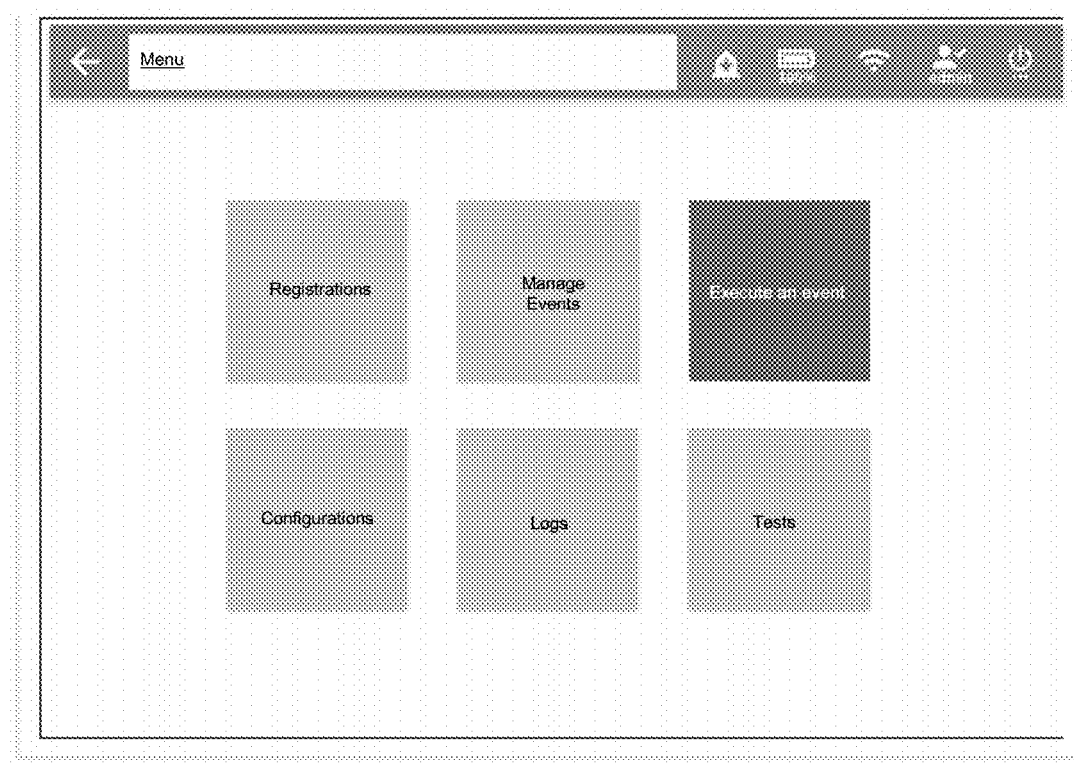
FIG. 4 shows a diagram of an embodiment of the operation of the software implemented in the processor (11) of the integrating means (10), and FIG. 4.a (Menu) shows the operating environments of the software; 4.b (Records), 4.c (Manage Events), 4.d (Perform an Event), 4.e (Settings), 4.f (Logs) and 4.g (Tests) show the environments for each functions available in the main menu.
Figure 4B:
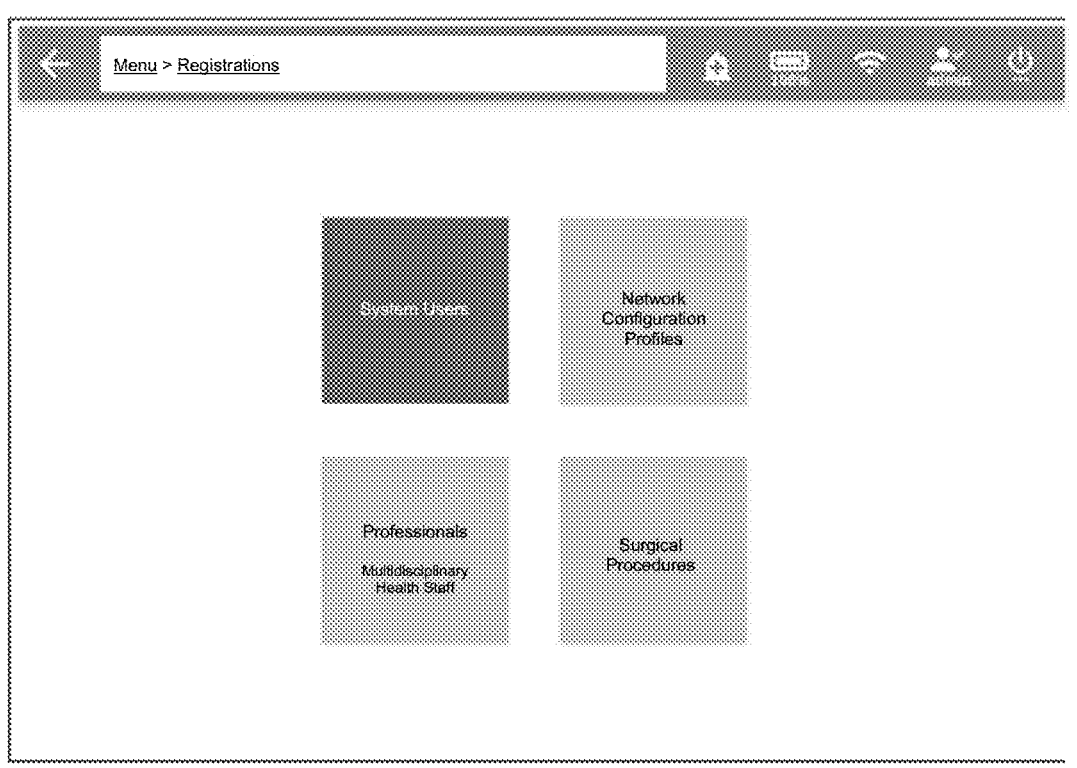
Figure 4C:
Figure 4E:
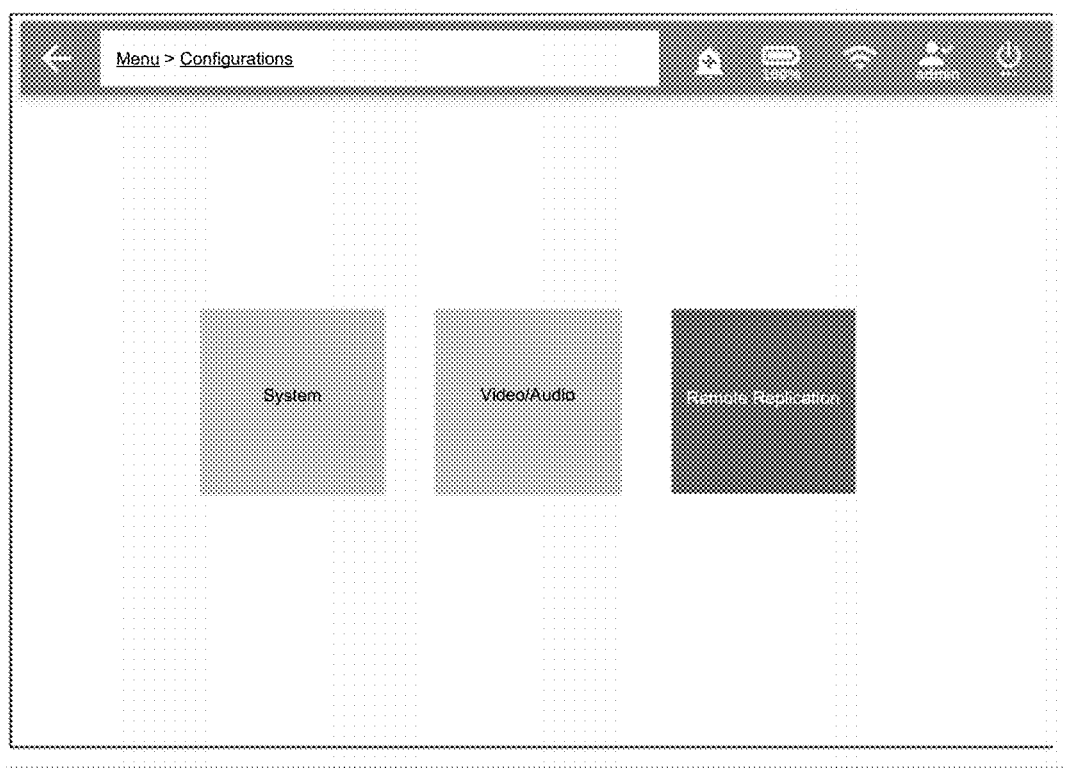
Figure 4F:
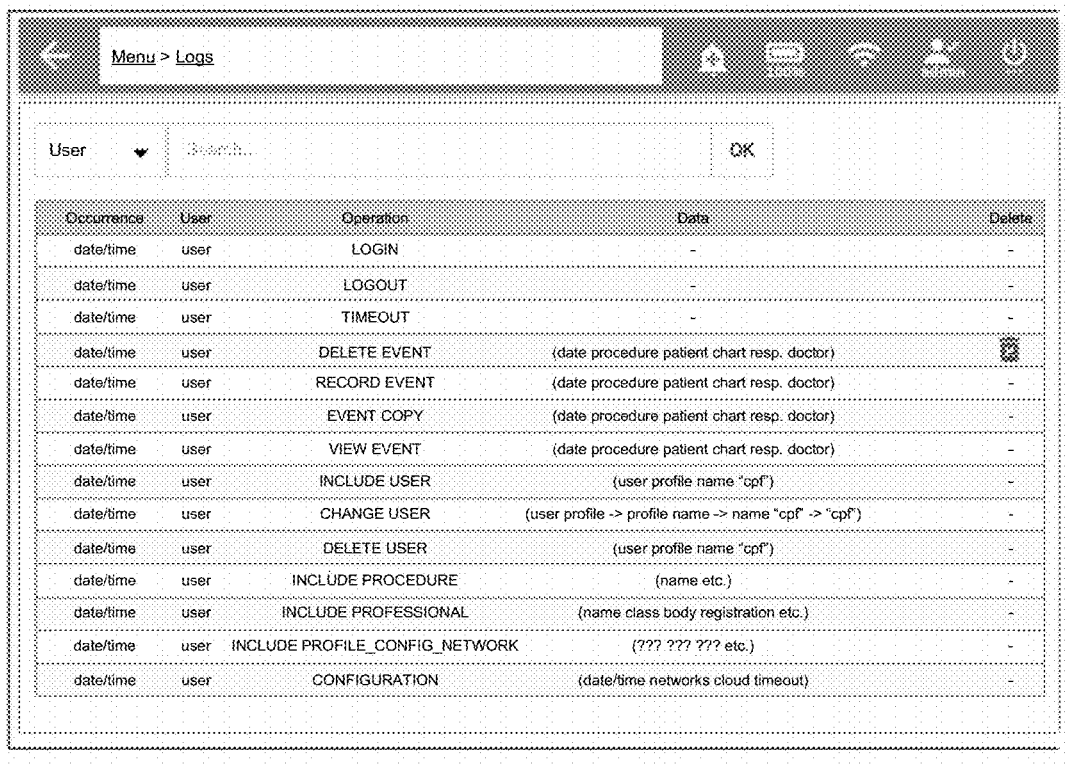
Figure 4G:
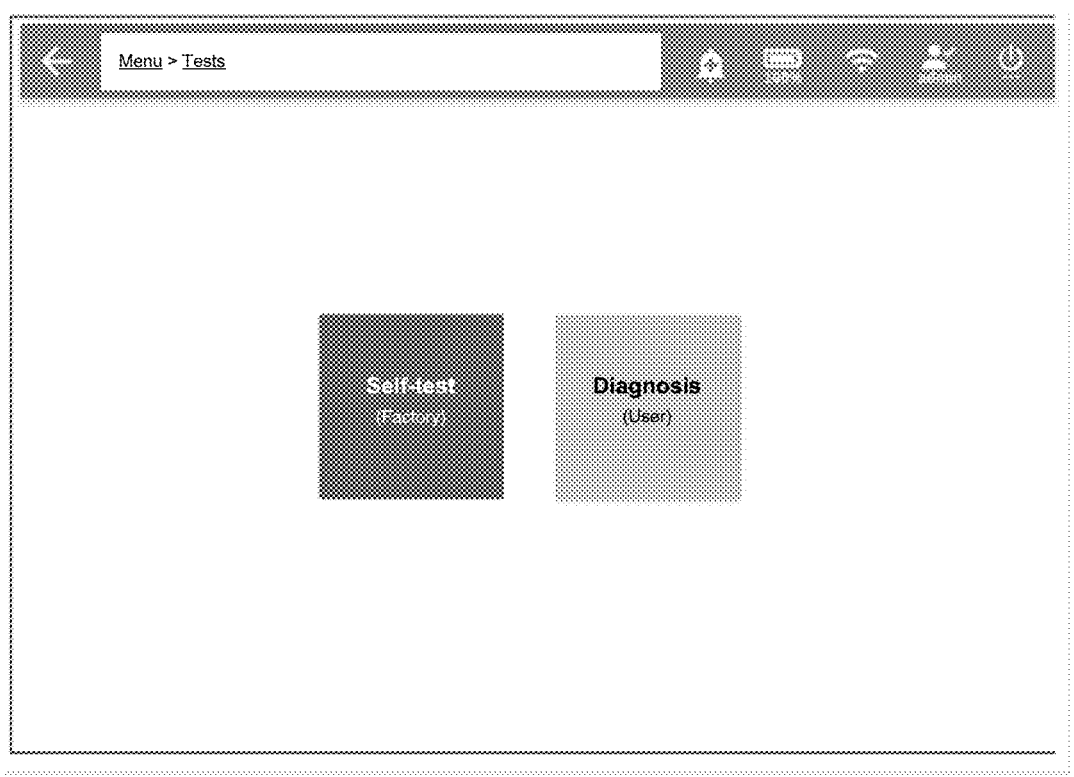
Figure 6:
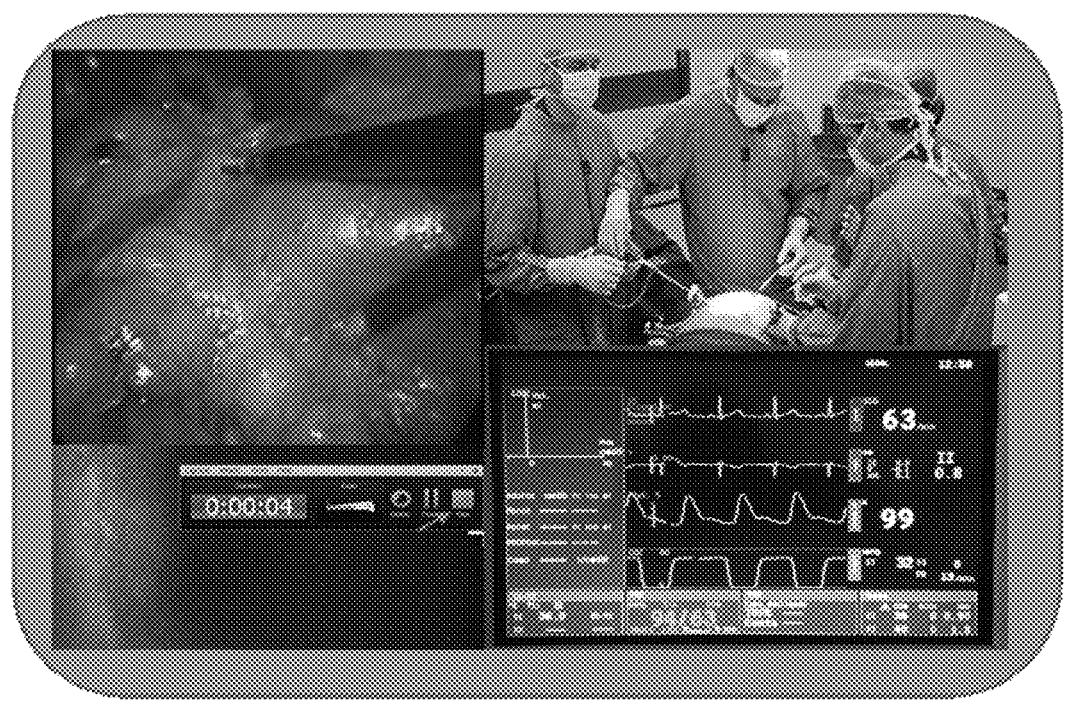
FIG. 6 shows one embodiment of a display containing graphically integrated surgical-surgical data.

FIG. 3 shows an example of the video image composed by the processor (11), where, in a full HD image, the laparoscopic camera video signal occupied a 1280×720 pixel block, the camera of the surgical environment occupied a 640×360 pixel block, the video signal of the vital signs monitor occupied a 640×360 pixel block, and the surgical event data occupied a 1920×360 pixel block. This generated video, which is made up of the resized images, was properly stored—locally (12) and remotely (30)—and reproduced by the image display (13). An example of the image generated by the processor can also be seen in FIG. 6.

Moreover, the system has a menu with the operating environments, being registrations, managing events, holding an event, configurations, logs and tests. In this sense, FIG. 4.a shows the Life Surgery Box menu with the various operating environments, wherein each of FIGS. 4.b, 4.c, 4.d, 4.e, 4.f and 4.g detail environments with their respective features.

Figure 5:
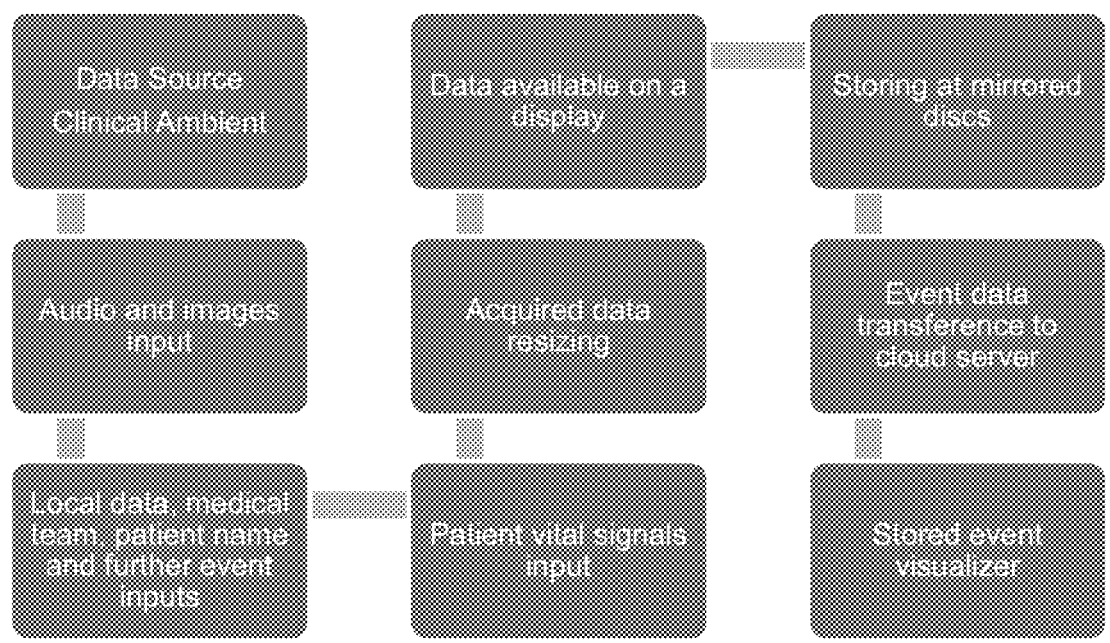
FIG. 5 shows a flowchart of one embodiment of the system's operation of the present invention.

Nevertheless, an example of operating modules of the processor (11) is shown in FIG. 5. As noted in this example, processor (11) resizes the clinical-surgical data and sends it to local storage (12), provided with a mirrored storage system, to forward it later to the remote storage (30) implemented in the cloud.

Thus, as mentioned above, the video signal generated by the processor (11) was stored locally (12) and, in parallel, reproduced on the image display (13). Upon completion of the surgical event, processor (11) is responsible for generating a video file and sending this file to the cloud storage (30). Once the file is completely transferred to the cloud (30), the processor automatically deletes the locally stored file (12) to free up local space for later applications. To ensure that the file has been completely transferred to the cloud (30), the processor (11) performs checksum routines, which check that the file has been fully transferred and, having the confirmation about the full transfer, the processor (11) deletes the local file.

The remote cloud storage (30) of the system, in turn, aims to store the data and make it available for viewing anywhere via a web browser (internet browser allowing visualization of the stored events—e.g. Google Chrome® or Firefox®). This component is a service for storing and streaming video on demand. The event transmission from the device to the cloud takes place automatically and therefore does not depend on the user.

Some functional features of the system are as follows: the system is capable of storing a large amount of recording hours; at the time of recording the storage is local, so that when the surgical procedure ends the data thereof is transferred to the cloud; the system has a local viewer or a cloud viewer via a browser (a web browser that allows the visualization of stored events—e.g. Google Chrome® or Firefox®); the system also has a means of capturing voice signals from the surgical environment; the local display has a signal indicating that recording has started and is in progress.

Also, the equipment signals when storage capacity is nearing its end. This warning is issued when there is X % (configurable) of the device's total recording capacity. The display shows an available capacity message nearing completion. The device allows snapshots (or photography) of the images being acquired by taking the specific interface for this purpose by means of the image capture element. The images can be used for documentation purposes and preparation of medical reports, already taking advantage of the images generated in the surgery. The image capture element is triggered by the operator by means of a pedal positioned next to it. The captured images are automatically exported in specific format according to the application, in this case being exported in the DICOM standard, facilitating the generation of the report.

Therefore, the system of the present invention makes it possible to record all data relating to the surgical environment, such as: the patient at the time of surgery, images of the entire patient surgical procedure, and data on how the patient behaves during surgery. This data provides a more realistic assessment of how the surgery was performed. This is important from several thinking perspectives:

The user can remember all the movements that happened during the surgery—through the video images of the surgery;

Correlation of surgery images with patient data at each moment of the procedure. This correlation provides extremely useful data so that each event, each maneuver and its repercussions in each phase of the surgery can be correlated;

The operating room environment has a considerable influence on the surgical act itself. Therefore, it is very important to also correlate the surgical environment with the maneuvers, each stage of the surgery and thus be able to evaluate the positive and negative repercussions on a given procedure. This provides a very interesting analysis on several aspects: critical evaluation, improvement and development of surgical techniques; correlate assertive maneuvers and maneuvers that require change, given their real evaluation of time and moment with the repercussions to the patient; and the importance for teaching, critical analysis, legal, ethical and patient safety improvement.

Those skilled in the art will appreciate the knowledge presented herein, and that such knowledge would enable one of skill in the art to make the invention in accordance with the embodiments disclosed and in other variants and alternatives within the scope of the following claims.

The invention claimed is:

1. A storage device, physically located at a clinical-surgical environment, for storing clinical-surgical data from at least one clinical-surgical event, the device comprising at least one processor and a local storage in communication with the at least one processor, the local storage comprises a memory device for storing data, wherein:
   the at least one processor is configured to receive clinical-surgical data from at least three signal sources of a plurality of signal sources connected to the storage device by means of a plurality of signal inputs arranged on the storage device;
   the at least one processor is configured to perform at least one resizing and composition block configured to integrate the clinical-surgical data received from said at least three signal sources into a single video image, which is interpreted by an image display also physically located in the clinical-surgical environment;
   the storage device comprises a redundant storage integrated in the storage device, the redundant storage also comprising a memory device for storing data and mirroring the data stored in the local storage;
   said plurality of signal sources comprise at least a surgical camera, a vital sign monitor video, a bispectral index (BIS) monitor, an operating room camera, and surgical event ambient audio of the clinical-surgical event;
   the plurality of signal inputs comprise an input or output selected from the group consisting of an analog laparoscopic surgical camera input, a digital laparoscopic surgical camera input, an analog vital sign monitor video input, a digital vital sign monitor video input, an analog operating room camera input, a digital operating room camera input, an IP operating room camera input, a surgical event ambient audio input, a bispectral index (BIS) monitor input, a USB touch screen monitor input, a USB microphone input, a foot pedal input, a display HDMI input, an external speaker output, or any combination thereof;
   the processor sends the clinical-surgical data simultaneously to the local storage and to the redundant storage and in parallel the image display;
   the processor sends the clinical-surgical data to a remote storage in communication with the processor only after a finishing of the clinical-surgical event; and
   the processor is configured to acquire a frame from the single video image when the processor receives a command signal from a foot pedal, the foot pedal also being physically located in the clinical-surgical environment, near to the operator and being in communication with the storage device, wherein the foot pedal is triggered by the operator during a clinical-surgical event in the clinical-surgical environment, and the acquired frame is sent by the processor to the local storage in a separate file, which is used for further medical reporting and/or learning purposes.

2. The storage device for storing clinical-surgical data of claim 1, wherein said local storage is configured to receive and store clinical-surgical data received from the processor.

3. The storage device for storing clinical-surgical data of claim 2, wherein the redundant storage is capable of storing data received from the processor.

4. The storage device for storing clinical-surgical data of claim 1, further comprising an image capture element adapted for capturing images provided in the image display, wherein said image capture element is implemented in the processor, and wherein said image capture element performs acquisition of one or more frames displayed in the image display.

5. The storage device for storing clinical-surgical data of claim 1, wherein the processor comprises a logger capable of identifying and storing actions performed by users who operate the storage device.

6. The storage device for storing clinical-surgical data of claim 1, further comprising at least one safety locking mechanism for increasing a security level needed by a user of the storage device to enable the user to access the storage device.

7. A system for storing clinical-surgical data from at least one clinical and surgical event, the system comprising a storage device, physically located at a clinical-surgical environment, for storing clinical-surgical data from at least one clinical-surgical event, the device comprising at least one processor and a local storage in communication with the at least one processor, the local storage comprises a memory device for storing data, wherein:
   the at least one processor is configured to receive clinical-surgical data from at least three signal sources of a plurality of signal sources connected to the storage device by means of a plurality of signal inputs arranged on the storage device;
   the at least one processor is configured to perform at least one resizing and composition block configured to integrate the clinical-surgical data received from said at least three signal sources into a single video image, which is interpreted by an image display also physically located in the clinical-surgical environment;
   the storage device comprises a redundant storage integrated in the storage device, the redundant storage also comprising a memory device for storing data and mirroring the data stored in the local storage;
   said plurality of signal sources comprise at least a surgical camera, a vital sign monitor video, a bispectral index (BIS) monitor, an operating room camera, and surgical event ambient audio of the clinical-surgical event;
   the plurality of signal inputs comprise an input or output selected from the group consisting of an analog laparoscopic surgical camera input, a digital laparoscopic surgical camera input, an analog vital sign monitor video input, a digital vital sign monitor video input, an analog operating room camera input, a digital operating room camera input, an IP operating room camera input, a surgical event ambient audio input, a bispectral index (BIS) monitor input, a USB touch screen monitor input, a USB microphone input, a foot pedal input, a display HDMI input, an external speaker output, or any combination thereof;

the processor sends the clinical-surgical data simultaneously to the local storage and to the redundant storage and in parallel the image display;

the processor sends the clinical-surgical data to a remote storage in communication with the processor only after a finishing of the clinical-surgical event;

the processor is configured to acquire a frame from the single video image when the processor receives a command signal from a foot pedal, the foot pedal also being physically located in the clinical-surgical environment, near to the operator and being in communication with the storage device, wherein the foot pedal is triggered by the operator during a clinical-surgical event in the clinical-surgical environment, and the acquired frame is sent by the processor to the local storage in a separate file, which is used for further medical reporting and/or learning purposes;

the storage device is in communication with the at least three signal sources of the plurality of signal sources, the plurality of signal sources being physically located in the clinical-surgical environment; and the processor sends a single file comprising the clinical-surgical data to the remote storage after completion of the clinical-surgical event and deletes a stored single file stored in the local storage and in the redundant storage after the single file is completely sent to the remote storage, and the processor acquires at least one frame from the single video image of the single file made available on the image display by means of a foot pedal in communication with the processor, wherein the foot pedal sends a command signal to the processor when the foot pedal is triggered by the operator, which sends a command signal from the foot pedal to the processor, wherein the at least one frame generated is sent by the processor to the local storage in a separated file, which can be used for further medial reporting and/or learning purposes.

8. The system for storing clinical-surgical data of claim 7, wherein the remote storage is configured to enable remote viewing of the composite clinical-surgical signal via a web browser.

9. A process for storing clinical-surgical data from at least one clinical-surgical event comprising the steps of:
a) receiving clinical-surgical data by at least one processor arranged in a data storage device physically located at a clinical-surgical environment, the clinical-surgical data being video signals, the clinical-surgical data originating from at least three signal sources of a plurality of signal sources, said plurality of signal sources comprising at least a laparoscopic surgical camera, a vital sign monitor video, a bispectral index (BIS) monitor, an operating room camera, and surgical event ambient audio of the clinical-surgical event;
b) in the processor, performing at least one resizing and composition algorithm that resizes and composes the received clinical-surgical data into a resizing and composition block configured to integrate the video signals of the clinical-surgical data received from said at least three signal sources and composing into a single file formed by a single video image;
c) with the processor, sending the single file simultaneously to a local storage and to a redundant storage and in parallel to an image display also physically located in the clinical-surgical environment and connected to the storage device, allowing the single file to be made available on the image display so that an operator can consult the single file, and to be stored in the local storage and in the redundant storage at the same time, wherein the processor sends the single file comprising the clinical-surgical data to a remote storage only after a finishing of the clinical-surgical event; and
d) acquiring, with the processor, at least one frame from the single video image of the single file made available on the image display by means of a foot pedal in communication with the processor, wherein the foot pedal sends a command signal to the processor when the foot pedal is triggered by the operator, which sends a command signal from the foot pedal to the processor, wherein the at least one frame generated is sent by the processor to the local storage in a separated file, which can be used for further medial reporting and/or learning purposes.

10. The process for storing clinical-surgical data of claim 9, further comprising the step of:
in the processor, identifying user profiles based on access levels.

11. The process for storing clinical-surgical data of claim 10, further comprising the step of:
in the processor, performing log generation from a task performed by a user, the log generation being linked to the identified user profile.

12. The process for storing clinical-surgical data of claim 9, further comprising the step of:
with the processor, capturing photographic images provided on the image display, wherein the capturing step is performed upon at least one of: i) automatically by the processor, based at least in part on a previously defined configuration of the processor; and ii) by an operator sending a command signal to the processor.

13. The process for storing clinical-surgical data according to claim 9, wherein the processor sends the composite clinical-surgical signal to the remote storage after the end of the clinical-surgical event.

14. The process for storing clinical-surgical data of claim 9, further comprising the step of:
generating an alarm when the processor detects at least one of: i) a proximity of storage capacity depletion of the local storage; and at least one of ii) a failure of the local storage, a redundant local storage; and transferring the clinical-surgical data to remote storage.

* * * * *